(12) United States Patent
Casset

(10) Patent No.: US 7,792,574 B2
(45) Date of Patent: Sep. 7, 2010

(54) ALERT PREDICTIVE OF DEGREDATION OF A PATIENT'S CLINICAL STATUS FOR AN ACTIVE IMPLANTABLE MEDICAL DEVICE AS FOR PACING, RESYNCHRONIZATION, DEFIBRILLATION AND/OR CARDIOVERSION

(75) Inventor: Cyrille Casset, Ris-Orangis (FR)

(73) Assignee: ELA Medical S.A.S., Montrouge (FR)

( * ) Notice: Subject to any disclaimer, the term of this patent is extended or adjusted under 35 U.S.C. 154(b) by 481 days.

(21) Appl. No.: 11/764,141

(22) Filed: Jun. 15, 2007

(65) Prior Publication Data

US 2007/0293736 A1    Dec. 20, 2007

(30) Foreign Application Priority Data

Jun. 15, 2006    (FR) .................................. 06 05322

(51) Int. Cl.
     *A61B 5/04*      (2006.01)
(52) U.S. Cl. ......................................... 600/513; 607/18
(58) Field of Classification Search .................. 607/18; 600/513
See application file for complete search history.

(56) References Cited

U.S. PATENT DOCUMENTS

| | | | |
|---|---|---|---|
| 5,304,208 A | 4/1994 | Inguaggiato et al. | |
| 5,342,404 A | 8/1994 | Alt et al. | |
| 5,454,838 A | 10/1995 | Vallana et al. | |
| 5,496,351 A | 3/1996 | Plicchi et al. | |
| 5,722,996 A | 3/1998 | Bonnet et al. | |
| 6,171,256 B1 * | 1/2001 | Joo et al. | 600/508 |
| 6,246,910 B1 | 6/2001 | Bonnet et al. | |
| 6,336,048 B1 | 1/2002 | Bonnet | |
| 6,604,002 B2 | 8/2003 | Molin | |
| 6,725,091 B2 | 4/2004 | Dal Molin | |
| 6,980,851 B2 * | 12/2005 | Zhu et al. | 600/513 |
| 2003/0040776 A1 | 2/2003 | Kroll et al. | |
| 2005/0131470 A1 * | 6/2005 | Vitali et al. | 607/9 |

(Continued)

FOREIGN PATENT DOCUMENTS

EP      0515319      11/1992

(Continued)

*Primary Examiner*—George R Evanisko
*Assistant Examiner*—Andrew Hayes
(74) *Attorney, Agent, or Firm*—Orrick Herrington & Sutcliffe, LLP

(57) ABSTRACT

An active implantable medical device, notably for pacing, resynchronization, defibrillation and/or cardioversion of the heart, or for diagnosis of a patient's condition, able to produce a predictive alert in response to a detected degradation of the patient's clinical status. The device measures and analyses (56) a parameter representative of the patient's metabolic needs, such as minute ventilation (MV), and a physical activity parameter, such as acceleration (G). It further diagnoses heart failure by evaluating an index of the patient's clinical status through applying a set of status criteria (S1, S2). It further measures and analyzes (56) a hemodynamic parameter such as endocardial acceleration (PEA) or intracardiac impedance, representative of the patient's myocardium contractility. An index of cardiac contractility is created and evaluated through applying a set of contractility criteria (S'1, S'2). A cross-analysis is then performed to provide a composite preventive alert signal as a function of the respective values taken by the clinical status and cardiac contractility indices. This signal can have different levels according to whether the sets of criteria have, or not, triggered an alert relating to the clinical status or cardiac contractility.

14 Claims, 4 Drawing Sheets

U.S. PATENT DOCUMENTS

2005/0240233 A1* 10/2005 Lippert et al. .................. 607/6
2006/0094967 A1    5/2006 Bennett et al.

FOREIGN PATENT DOCUMENTS

| EP | 0582162 | 2/1994 |
| EP | 0655260 | 5/1995 |
| EP | 0750920 | 1/1997 |
| EP | 0919255 | 6/1999 |
| EP | 0966987 | 6/1999 |
| EP | 1116497 | 7/2001 |
| EP | 1138346 | 10/2001 |
| EP | 1533001 | 5/2005 |

* cited by examiner

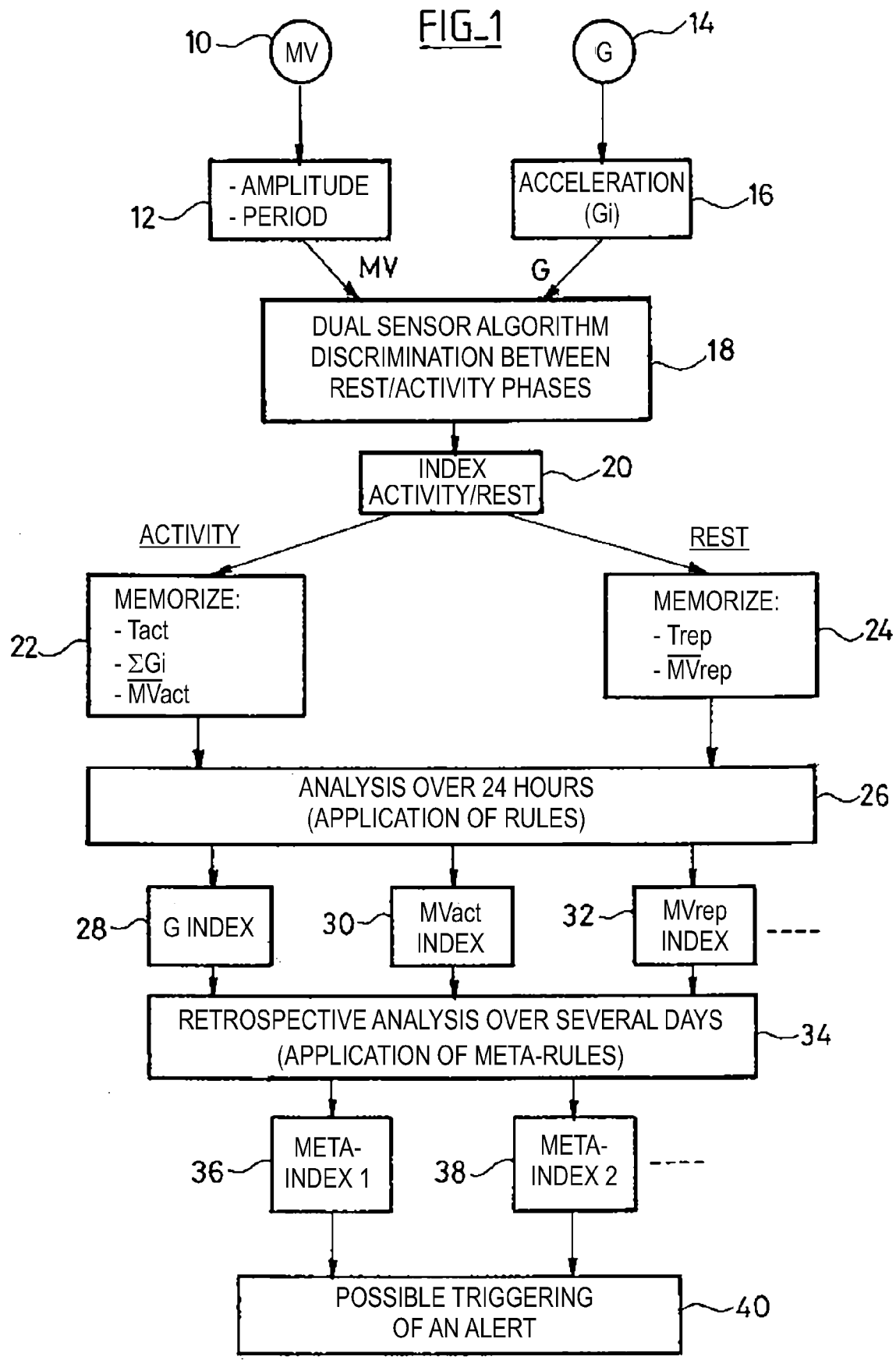

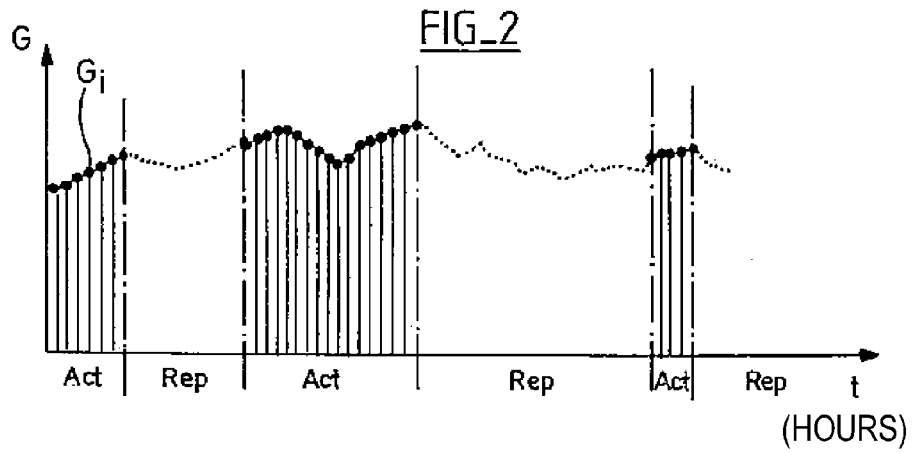
FIG_2
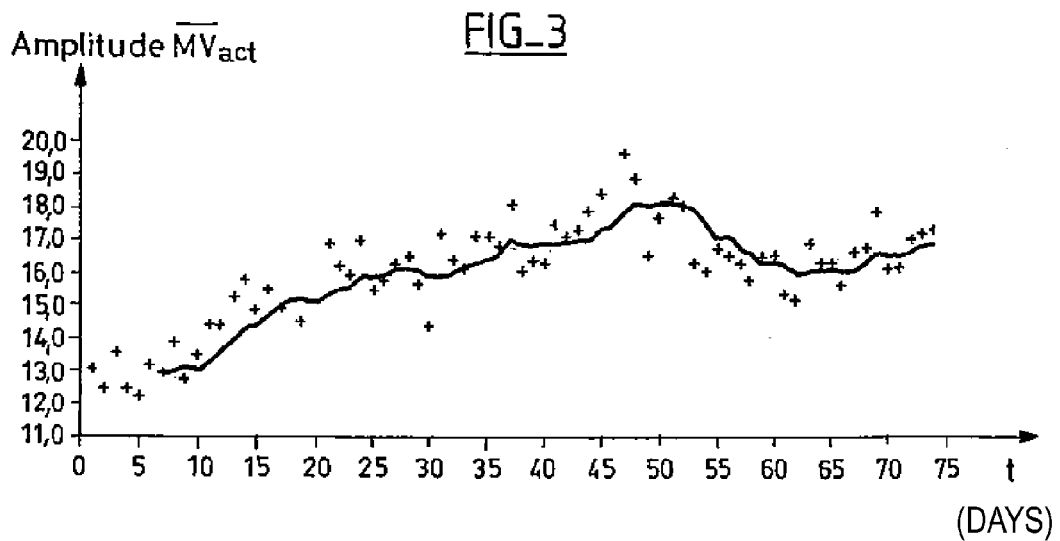
FIG_3
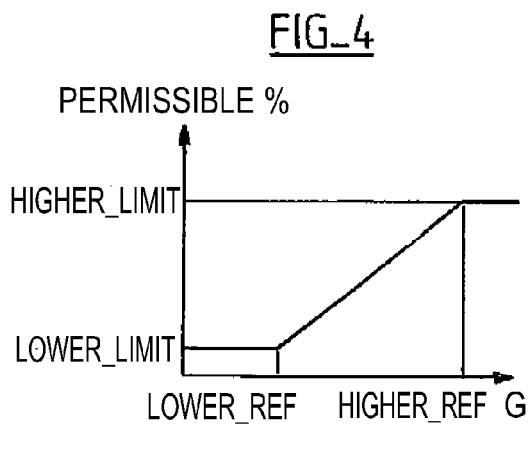
FIG_4
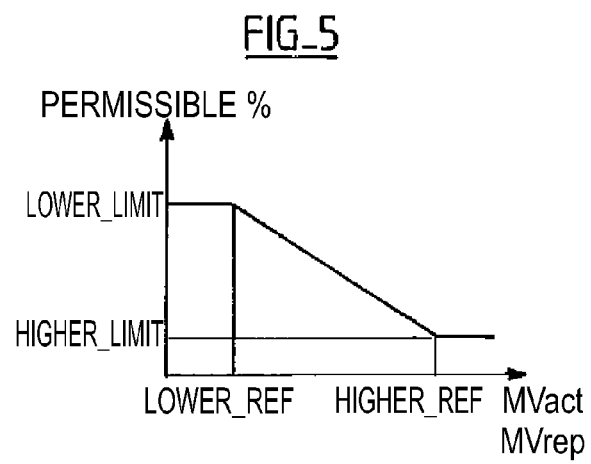
FIG_5

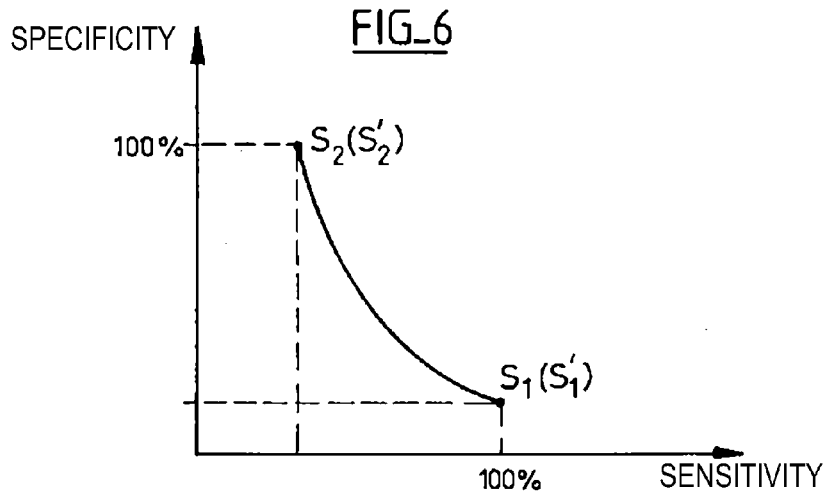
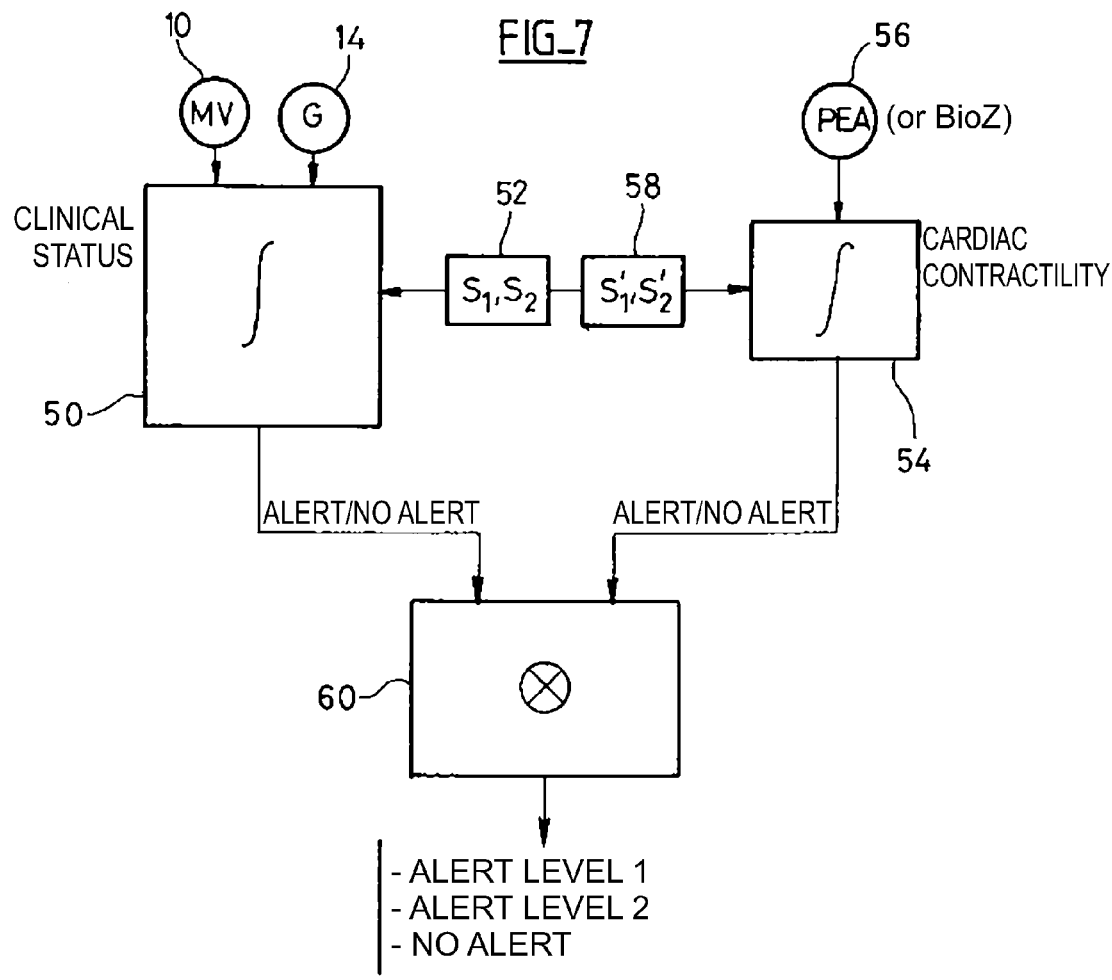

FIG_8
| ALERT SIGNAL | | CARDIAC CONTRACTILITY | | |
|---|---|---|---|---|
| | | NO ALERT | ALERT LEVEL $S_1$ | ALERT LEVEL $S'_2$ |
| CLINICAL STATUS | NO ALERT | NO ACTION | NO ACTION | ALERT 1b |
| | ALERT LEVEL $S_1$ | NO ACTION | ALERT 1 | ALERT 2b |
| | ALERT LEVEL $S_2$ | ALERT 1a | ALERT 2a | ALERT 2 |
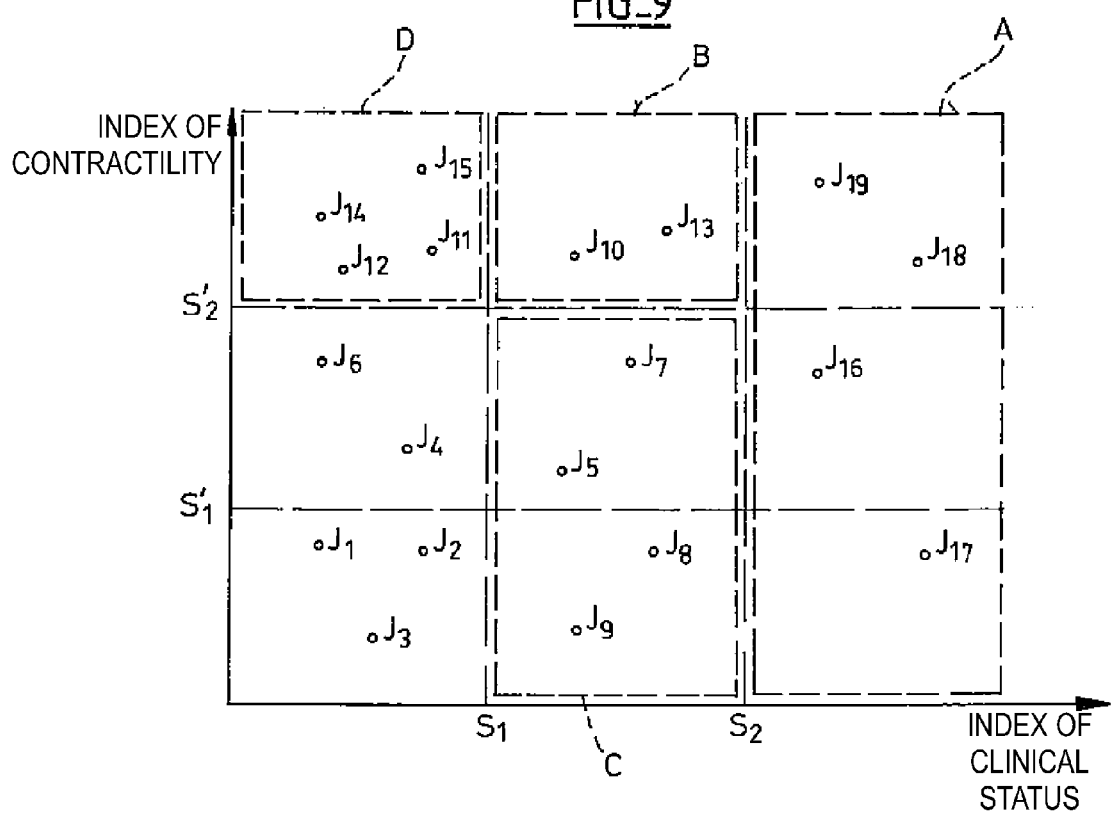
FIG_9

ALERT PREDICTIVE OF DEGREDATION OF A PATIENT'S CLINICAL STATUS FOR AN ACTIVE IMPLANTABLE MEDICAL DEVICE AS FOR PACING, RESYNCHRONIZATION, DEFIBRILLATION AND/OR CARDIOVERSION

FIELD OF THE INVENTION

The present invention relates to "active implantable medical devices" as such devices are defined by the Jun. 20, 1990 Directive 90/385/CEE of the Counsel of the European Community, and more particularly to cardiac pacemakers, resynchronization, cardioverters and/or defibrillators intended for the treatment of heart disorders, or to active implantable devices intended for diagnosis of heart disorders. It is more particularly related to devices having an operation enslaved (i.e., responsive) to parameters collected by sensors that allow one to assess the metabolic needs of the patient, as well as the patient's current level of activity.

BACKGROUND OF THE INVENTION

A patient's heart rate can be used for controlling a pulse generator, but this parameter is not directly representative of the patient's metabolic needs nor of his instantaneous physical activity.

Enslaved devices are known for use in controlling a pulse generator. Such devices typically have two different kinds of sensors, i.e. one sensor for the measurement of a corporal parameter that is predominantly physiologic, and one sensor for the measurement of a corporal parameter that is predominantly physical. One will hereinafter refer to the particular example of a minute-ventilation (MV) sensor as the physiologic sensor, corresponding to the most usual case, but it should be understood that this example is in no way limitative of the invention, and other types of sensors that provide a signal representative of the patient's metabolic needs (for example, a sensor that is measuring blood oxygen saturation) or his hemodynamic status (for example an intracardiac bio-impedance sensor) may equally be used.

Likewise, one will hereinafter refer to the particular example of an acceleration (G) sensor as the physical (activity) sensor, corresponding to the most usual case, but again, it should be understood that other types of sensors can be considered, notably to detect the patient's movements in the alternative. Generally, the physical (activity) sensor is characterized by a response time that is shorter than that of the physiological sensor, in order to allow a very fast detection of short-duration activity, before the activity is recognized through a significant change of the physiological parameter, which varies more slowly.

European patent EP 0750920, and its counterpart U.S. Pat. No. 5,722,996, commonly assigned herewith to ELA Medical, describe a device that is enslaved to two sensors, an MV sensor and a G sensor operating a selection of one sensor or the other so as to take into account only that sensor which gives the more relevant signal at any given moment. European patent EP 0919255 and its counterpart U.S. Pat. No. 6,336,048, also commonly assigned herewith to ELA Medical, describe an enslavement based upon the use of a combination of the signals provided by these two sensors. The signals delivered by these sensors can be used for controlling the application of pacing pulses to the patient, as part of an antibradycardiac therapy or for preventing syncopes of vasavagal origin. European patent EP 1533001 and its US counterpart published application US 2005/0131470 (commonly assigned herewith to ELA Medical), and published US patent application US 2003/0040776 (Kroll, Sorensen, Bornzin) describe devices designed for such applications.

Another application of the signals delivered by the physical and physiologic sensors operates a diagnosis of heart failure (CHF), notably in order to act on the pulse generator programming in an appropriate and preventive manner.

The present invention particularly concerns such devices with means for diagnosing heart failure.

Thus, the European patent EP 0966987 and its U.S. counterpart patent U.S. Pat. No. 6,246,910, commonly assigned herewith to ELA Medical, propose a device that allows one to follow the evolution of the patient's condition over time so as to give an adequate representation of actual metabolic requirements thereof, i.e., taking into account the actual activity level of the patient. The device described in that document adjusts its operation in case of a worsening or an improvement of the patient's status, for example, by reprogramming selected device functions, in order to follow the evolution of the patient's clinical status and to adapt to his effective cardiac decompensation level.

It has been recognized that patients, though actually implanted with the aforementioned devices, are adapting their own daily activity to the changes in their clinical status, with an incidence on their activity level, and, in some cases, on their respiratory status. Indeed, the clinical modifications being likely to be asymptomatic, it is usual that the patient unconsciously adapts his activity to his clinical status: the first crisis of heart failure appearing during activity, the patient is led to reduce his activity in order to avoid a reoccurrence of such crisis. Then, although the symptoms no longer occur because the patient changed his behavior so as to prevent them, the pathology keeps on evolving. As a result, the patient's heart failure will eventually disturb him even when he is at rest and the patient will need to visit his physician again, or worse seek emergency care.

Due to such an auto-adaptation, the absence of symptoms perceived by the patient leads to a significant delay between the onset of clinical modifications, to the actual diagnosis thereof, the latter being most often too late.

It has been proposed to utilize the information coming from the physical and physiologic sensors, so as to evaluate the real clinical status of the patient and the evolution of his pathology, even in the absence of actual symptoms felt by the patient, and even though the patient unconsciously adapts his behavior to the evolution of his clinical status (that is: even if he reduces his activity so as to prevent an occurrence of heart failure).

To that end, the device evaluates and updates, for example, on a daily basis, one or plural indices reflecting the clinical status of the patient. The evolution of these indices is analyzed by the device, which notably can deliver a preventive alert signal when a certain number of criteria are fulfilled that raises a suspicion of an aggravation of the patient's clinical status, even in the absence of any serious symptom. This alert allows one to take appropriate measures as soon as possible, thereby preventing from triggering an unexpected heart failure crisis within a short term.

One of the difficulties encountered with such type of an analysis lies in the parameterization of the different criteria for triggering the alert. The values taken by the different indices of clinical status are evaluated every day with respect to a set of plural criteria, comprising fixed parameters such as thresholds, incremental parameters such as minimum or maximum percentages of increase, metarules analyzing the evolution of the indices and their combination over several days, etc. Parameterization of this set of criteria (rules and metarules) can be modified so as to improve the sensitivity for triggering the alert or, conversely, for a better specificity of the triggering.

In the present description, it should be understood that sensitivity and specificity (i.e., selectivity) are two antagonist notions, as far as an increase of sensitivity is necessarily coupled with a lower specificity—with a correlative increase of the risk of false alert. Reciprocally, an increase of specificity will be detrimental to sensitivity—with a correlative risk for not triggering the alert in critical cases. In other words, the stricter the alert criteria, the fewer cases of false positives, but as a consequence, the risks of false negatives increase. Reversely, if one wishes to reduce the cases of false alerts, there is a correlative risk of missing some justified alerts.

OBJECTS AND SUMMARY OF THE INVENTION

The starting point of the present invention lies in the observation that, with the techniques already known in the prior art, the parameterization of the criteria for triggering an alert predictive of the degredation of a patient's clinical status implies a compromise between sensitivity and specificity.

Moreover, taking into account the multiplicity of the parameters involved in the triggering of the alert, it is difficult for the practitioner to evaluate the actual level of sensitivity and specificity of the device. The device's behavior in a given situation will thus be difficult to foresee, and even the practitioner can have difficulties in determining the relevancy of the device's reactions.

Finally, the delivered alert being of the "all or none" type, and provided the risks of false positives, there is a risk that the patient gets uselessly alerted in case of triggering of an alert, which does not provide him any means for evaluating the actual level of the risk of which he is being warned. Although, certain evolutions of the pathology require an action with no delay (i.e., urgent care for the patient from the physician or an emergency medical visit), whereas some others simply reveal a slow degradation of the patient's status, with a lower risk, not requiring urgent care or hospitalization.

One aspect of the present invention is directed to a device of the general type described in EP 0966987 and corresponding U.S. Pat. No. 6,246,910 cited above, which disclosure is incorporated herein by reference, including means for diagnosing heart failure, means for measuring a corporal parameter that is predominantly physiologic, preferably the minute ventilation, and providing a physiologic signal; means for measuring a corporal parameter that is predominantly physical, notably the acceleration, and providing a physical signal; means for discriminating between rest and activity phases, operating in response to said physiologic and physical signals, and providing an indication of the patient's activity; means for evaluating a clinical status of the patient, able to determine at least one clinical status index by applying at least one set of status criteria (S1, S2) to the signal of metabolic need, the physical signal and the activity index.

In accordance with the present invention, with the objective to solve the problems and palliate the limitations referred to above, the means for diagnosing heart failure further includes means for measuring a hemodynamic parameter, delivering a hemodynamic signal representative of the myocardium contractility; means for evaluating cardiac contractility, able to deliver at least one index of cardiac contractility through applying at least one set of contractility criteria (S'1, S'2) to the hemodynamic signal, and means for cross analysis, receiving as input the index (indices) of clinical status, the index (indices) of cardiac contractility, and delivering as output a composite preventive alert signal that is function of the respective values of the indices of clinical status and cardiac contractility.

BRIEF DESCRIPTION OF THE INVENTION

Further features, characteristics and advantages of the present invention will become apparent to a person of ordinary skill in the art in view of the following detailed description of preferred embodiments of the invention, made with reference to the attached drawings, in which the same number references designate identical or functionally similar elements from one figure to the next, and in which:

FIG. 1 is a block schematic showing the functionality of a device in accordance with the present invention determining the clinical status indices as part of a predictive diagnosis;

FIG. 2 shows variations of the acceleration signal taken into account by the device of FIG. 1;

FIG. 3 shows the variations of the average minute ventilation in activity, over a period of several weeks;

FIG. 4 shows the transfer function for the determination of the clinical status indices relating to the acceleration and the time spent in activity;

FIG. 5 shows the transfer function for the determination of the clinical status indices relating to the minute ventilation in activity and at rest;

FIG. 6 is a chart showing the sensitivity/specificity duality with different possible choices for the sets of analysis criteria;

FIG. 7 is a block schematic showing the functions involved in the analysis technique in accordance with the present invention.

FIG. 8 is a truth table showing the different levels of alert produced by the device of FIG. 1 as a function of the respective values that can be taken by the clinical status alert signals and cardiac contractility signals; and FIG. 9 shows the distribution in a bidimensional space, of the daily values taken by the indices of clinical status and cardiac contractility, in a way illustrating the different risk zones, and the way the device of the invention is reacting as a function of daily evolution of these indices.

One will now describe a preferred embodiment of the device of the present invention. Regarding the software-related aspects thereof, it should be understood that the invention can be implemented by means of an appropriate programming of the software of a known enslaved pacemaker. The present invention can preferably be applied to the implantable devices marketed by ELA Medical, Montrouge, France, such as the Symphony and ELA Rhapsody brand pacemakers. These devices are equipped with programmable microprocessors, including circuits intended to acquire, format and process electrical signals collected by implanted electrodes and various sensors. It is also possible to upload to these devices, by telemetry, pieces of software that will be stored in internal memory and run so as to implement the features of the invention, described in more detail below. Implementing the features of the present invention into these devices is believed to be easily within the abilities of a person of ordinary skill in art, and a matter of design or implementation choice, and will therefore not be described in detail herein.

With reference to FIG. 1, the device includes a sensor 10 providing a signal that is representative of the patient's metabolic demand, typically a transthoracic impedance signal, the analysis of periodical variations thereof (amplitudes and successive periods) being performed by block 12 that provides a minute ventilation (MV) signal. The device also has a physical sensor that senses the patient's movements, typically an acceleration sensor 14 associated with a sampling circuit 16 providing a succession of digitized samples Gi with a sampling step i=125 ms for instance.

Based upon concurrently provided MV and G information, the device performs an enslavement of the "dual sensor" type (block 18) as described in EP A 0750920 and U.S. Pat. No. 5,722,996, and EP A 0919255 and U.S. Pat. No. 6,336,048 referred to above, preferably a control of pacing rate and eventual adapting of operating parameters. That enslavement function is not per se part of this invention, is known in the art, and will not be described in detail in this document.

However, the enslavement algorithm has the advantage of comprising a discrimination function, between phases of activity and phases of rest of the patient (block 18), based upon instantaneous indications from the MV and G sensors, resulting in a status indicator 20 that is able to take at least two values, namely "activity" and "rest" (some other values being possible, for example, "recovery after exercise", that will be assumed to be an activity phase, or "sleep" which is a particular case of rest phase).

The device stores the data provided by MV and G sensors into the device memory, in distinct ways for the activity and rest phases.

For the characteristic parameters in the activity phase, the device memorizes (block 22):
 the time elapsed in activity phase over the last 24 hours (Tact),
 the sum of the measurements of G sensor in activity phase: $\Sigma G_i$, and
 the mean minute ventilation ($\overline{MV}_{act}$) during the activity phases, measured over the last 24 hours.

FIG. 2 shows more precisely the way that the data $\Sigma G_i$ is obtained and updated.

As stated above, the G sensor provides a series of digitized samples $G_i$ with sampling step intervals of i=125 ms, for example, of which the variations over time are shown in FIG. 2.

Also, status indicator 20 allows one to distinguish between activity phases (Act) and rest phases (Rep). The device proceeds to the summing of the values $G_i$ of the samples over the last 24 hours, but inhibits that summing during rest phases, thus only summing values corresponding to periods of activity.

As for $\overline{MV}$ act parameter, it is a mean value of minute ventilation MV during activity periods. FIG. 3 shows as an example, the variations of that parameter $\overline{MV}$ act over time, over a duration of several weeks. The plus signs indicate the values that are computed daily, and memorized, the solid line indicates a moving average over 7 days.

For the characteristic parameters in the rest phase, the device memorizes (block 24):
 the time elapsed at rest over the last 24 hours (Trep), and
 the mean minute ventilation ($\overline{MV}$rep) during rest phases, measured over the last 24 hours.

The $\overline{MV}$ rep parameter is a mean value of minute ventilation during rest phases.

These various pieces of information are memorized and updated in the value tables of blocks 22 and 24, and then subjected to an analysis (block 26) that applies a certain number of inference rules providing a series of clinical status indices, such as notably:
 an index 28 related to the acceleration (index G),
 an index 30 related to the minute ventilation in activity (index MVact),
 an index 32 related to the minute ventilation at rest (index MVrep).

This analysis is, for example, operated every day, with daily update of the various clinical status indices. Other periods for the analysis could be used and the notion of a period could include a predetermined number of cardiac contractions.

Plural analysis methods are possible. A first method is directed to comparing the memorized values with various fixed references, and to detect the crossing of high and/or low thresholds.

A second and preferred method, described below, involves analyzing the variations of data from one day to the next (or over another period, for instance from one week to the following week, etc.), and comparing this variation to a reference value corresponding to a percentage of variation that is physiologically permissible, taking into account the clinical status of the patient. The crossing of this limit will reveal a degradation of the patient's clinical status with respect to the corresponding criterion (activity, basal ventilation, etc.).

One will now describe in detail, for example, the inference rule corresponding to the G criterion, and it should be understood that the rules corresponding to the other criteria are applied in a similar manner.

The memorized parameters relating to activity phases contain a series of values Sum_G(i), the step i corresponding here to a one-day interval. Instead of applying the inference rule to an isolated daily value, a moving average is preliminarily calculated over one week, so as to weight the activity variations from one day to the next, that average being expressed as follows:

$$M7G(i) = (1/7) * \sum_{k=i-6}^{i} \text{sum\_G}(k)$$

The rule relating to the G parameter will be referred to as "Rule R1", and the result of its application will be an index able to take three values, representative of the evaluation of the patient's clinical status as regard to that G parameter: +1 (improvement), −1 (degradation), or 0 (stability).

Indeed, the increase of activity is a favorable element in the patient's clinical picture, which justifies the "+1" score, whereas a reduction of his activities is on the contrary, an unfavorable element from a long-term point of view.

These values are attributed as follows:

Rule R1:

If $M7G(i) > M7G(i-6)*[1+\alpha(M7G(i))]$, then R1(i)=+1

If $M7G(i) < M7G(i-6)*[1+\alpha(M7G(i))]$, then R1(i)=−1 else R1(i)=0

$\alpha(M7G(i))$ being a percentage calculated based upon a transfer function depending on the current value of the considered criterion.

The point of a non-constant $\alpha$ factor is related to the necessity for taking into account the previous results in order to qualify the improvement or degradation of the result: hence, for a patient with a very low activity, an increase in activity, even if moderate, will be a very favorable element, which is not necessarily the case for a patient with a sustained activity in regular increase.

FIG. 4 shows the transfer function providing the permissible increase rate (hereinafter referred to as Parameter- Threshold) as a function of the value of the considered parameter. In the previous example with the parameter G, the transfer function is defined as follows:

ParameterThreshold(M7(i))=Lower_Limit if M7(i) <Lower_Ref;

ParameterThreshold(M7(i))=Higher_Limit if M7(i) >Higher_Ref

ParameterThreshold(M7(i))=A*M7(i)+B,

A, B being the slope and intercept point of the straight line going through the points (Lower_Ref, Lower_Limit) and (Higher_Ref, Higher_Limit).

The principle of this transfer function is also applicable, mutatis mutandis, to the time elapsed in activity Tact.

However, as to the ventilation parameter, in activity ($\overline{MV}$act) or at rest ($\overline{MV}$rep), the direction of variation of the transfer function shall be reversed, as illustrated on FIG. 5. Indeed, in the case when a patient presents a high rest ventilation, even a small increase is enough to strongly hinder him, whereas on the contrary, if he presents a lower ventilation, he has a larger margin of increase.

The results thus obtained through applying the various rules may be subjected to a deeper diagnosis, through the application of metarules, allowing one to define one or more indices of a higher level, or "meta-indices". These meta-indices are determined (block 34) by a retrospective analysis of the successive values taken by the different indices.

These metarules can be built up in various ways, and a simple example thereof will be given below, defining a limit over several days (p days) for which it is necessary that a rule R provides a minimum number of positive values of the corresponding index (this minimum being set to the value MR_Threshold):

Metarule MR (a "+1" value being representative of a significant aggravation of the patient's status):

$$MR(i) = \sum_{k=i-p+1}^{i} R(k),$$

with p being a natural integer

If MR(i)>MR_Threshold, then MR(i)=+1;

Else MR(i)=0

This metarule takes into account the fact to have null or negative index values: indeed, null values do not increase the value MR(i) of the meta-index, whereas negative values have the effect of "compensating" the positive values previously taken.

One thus obtains one or several meta-indices 36, 38, ... reflecting the evolution of one of the parameters G, $\overline{MV}$act, $\overline{MV}$rep, ... or a combination of these various parameters.

An alert can be triggered as a function of the results produced by the rules and metarules (block 40). This alert allows one to anticipate in an extremely premature way, prior to any serious symptom, the occurrence of an event such as heart failure crisis, in order to take necessary measures with no delay, so as to avoid the occurrence of this crisis, or at least reduce its effects, long before the patient has warned his practitioner or needs to seek emergency care.

But, in practice, the triggering or non-triggering of the alert may be influenced by events or particular situations that are not taken into account by the analysis technique described above.

First, if the cardiac decompensation has indeed an effect on the activity and/or ventilatory state of the patient—which the device actually detect, other events also can modify these clinical parameters, notably some pathologic situations that are not related to heart decompensation, such as an evolving cancer, pneumonia, influenza, ... The analysis is therefore not exclusively specific to heart decompensation and may be influenced by other pathologies of a completely different nature.

Secondly, the time constant of the analysis of activity and/or patient ventilatory state, and the potential triggering of an alert, are relatively long, typically a few days. Also, in certain situations of brutal cardiac decompensation (in 24 hours for instance), the reaction time will be too long for an alert to be delivered on time. Indeed, if the analysis described above is well adapted to situations of slow degradations, it does not take sufficiently into account the crisis situations implying a fast decrease of cardiac tonus.

The basic idea of this invention is to counteract these two drawbacks by combining the analysis of physiologic and physical parameters (MV and G) with the analysis of the variations of a hemodynamic signal, representative of the myocardium contractility and therefore very specific to cardiac decompensation.

In a characteristic manner, the device in accordance with the present invention to that end, includes in addition to the physiologic (MV) and physical (G) sensors, a hemodynamic sensor to evaluate the variations of contractility, which are correlated to the increases of blood pressure.

However, as compared to the MV or G signals, the information provided by the hemodynamic sensors has the drawback of being noisier and sensitive to many external factors such as the heart rate, the current activity, medication, etc.

In order to overcome this drawback, the device in accordance with the invention performs a crossed control between, on one hand, the information given by the MV and G sensors (representative of the patient's clinical status), and, on the other hand, the information given by the hemodynamic sensor (representative of cardiac contractility). That cross-control allows delivery of a relevant alert, adapted to each clinical case, with:

a better discrimination between the alerts related to cardiac decompensation and those induced by other causes (influenza, physical handicap, brutal change of habit, ... ), and a significant reduction of the time constant for triggering the alert, the device being able to react in an efficient way in the case of a brutal decrease of the cardiac tonus.

In addition, so as to improve the sensitivity/specificity ratio (that is to reduce both false positives and false negatives), the device can, in a preferred embodiment, advantageously utilize not one set of criteria but at least two sets of distinct criteria (by "set of criteria", one will refer to the whole of the rules and eventually the metarules, concurring to the triggering or non-triggering of an alert signal).

By applying these two (or more) sets of criteria to the collected signals, and by comparing the obtained results (alert/no alert) for each of these sets of criteria, the device will be able to perform an action that is even more adapted to the effective clinical situation of the patient.

FIG. 6 shows the duality of these two parameters: specificity/sensitivity in the choice of the sets of criteria: for the analysis of clinical status, one can thus choose a set of criteria S1 presenting a maximum sensitivity and a low specificity, and a set of criteria S2 presenting, reversely, a maximum specificity but a lower sensitivity. It is also possible to choose any other couple of sets of criteria {S1, S2} between those two extrema.

In the same way, for the analysis of cardiac contractility, one can choose two sets of criteria S'1 with a high sensitivity (and therefore low specificity) and S'2 with a high specificity (and therefore low sensitivity).

FIG. 7 schematically shows the implementation of a cross-analysis technique according to a preferred embodiment of the present invention. Block 50 represents a transfer function corresponding to all the steps described with reference to FIG. 1. This transfer function analyzes the patient's clinical status based upon the information provided by the physiological (MV) sensor 10 and physical (G) sensor 14.

Through applying two different sets of criteria {S1, S2} schematically illustrated at 52, the transfer function of block 50 produces, or does not produce, an output alert signal, and it does so distinctly for each of the two sets of criteria S1 and S2.

In the same way, a transfer function represented by block 54 evaluates the cardiac contractility based upon the signal provided by a hemodynamic sensor 56.

Through applying two different sets of criteria {S'1, S'2} schematically illustrated at 58, the transfer function of block 52 produces, or does not produce, an output alert signal, and it does so distinctly for each of the two sets of criteria S'1 and S'2.

The hemodynamic sensor 56 is advantageously an endocardial acceleration sensor of the PEA type (Peak Endocardial Acceleration) such as that described, for example, in European patents EP 0,515,319, EP 0,582,162 and EP 0,655,260 and their respective U.S. counterpart patents U.S. Pat. Nos. 5,304,208, 5,454,838 and 5,496,351 (assigned to Sorin Biomedica SpA). EP 0,515,319 teaches a way to collect an endocardial acceleration signal by means of an endocardial lead equipped with a distal pacing electrode implanted into the ventricle and integrating a microaccelerometer to measure the endocardial acceleration. EP 0,655,260 and U.S. Pat. No. 5,496,351 describes a way to process the endocardial acceleration signal provided by the sensor located at the tip of the lead, so as to compute two respective values of peaks of endocardial acceleration, corresponding to the two major noises that are likely to be identified in each beat of a healthy heart.

More precisely, the first endocardial acceleration peak ("PEA I") corresponds to the closure of mitral and tricuspid valves, at the beginning of the phase of isovolumetric ventricular contraction (systole). The variations of this first peak are closely related to pressure variations in the ventricle (the amplitude of PEA I peak, being more precisely correlated to the positive maximum of pressure variation, dP/dt, in the left ventricle) and can therefore be a representative parameter for myocardium contractility. The second peak of endocardial acceleration ("PEA II") corresponds to the closure of aortic and pulmonary valves, at the beginning of the diastole. It is produced by the brutal deceleration of moving blood mass in the aorta.

In another embodiment, the hemodynamic sensor 56 can be an intracardiac impedance sensor, for example, a sensor for measuring the bioimpedance (BioZ) as that described, for example, in European patents EP 1,116,497 or EP 1,138,346 and their respective U.S. counterpart patents U.S. Pat. Nos. 6,604,002 and 6,725,091 (commonly assigned herewith to ELA Medical).

EP 1,116,497 and U.S. Pat. No. 6,604,002 describes performing a dynamic bioimpedance measurement to evaluate the diastolic and systolic volumes, and to obtain an indication on the heart flow and therefore the ejection fraction. It more precisely describes a technique for the measurement of transvalvular bioimpedance (between the atrium and ventricle on the same side of the heart) through a tripolar configuration, with injection of a current pulse between an atrial site and a ventricular site, and collection of a differential potential between an atrial site and a ventricular site, with one of said sites common to the current injection and potential collection, one site dedicated to the current injection and one site dedicated to the potential collection. The injected current is a low-amplitude current, so as not to excite the cardiac cells.

EP 1,138,346 and U.S. Pat. No. 6,725,091 describes another type of measurement of bioimpedance, which is a transseptal bioimpedance, that is between a site at one side of the heart and a site at the other side. That technique also allows to deliver a value that is representative of the ejection fraction, even though the signal is weaker than in the case of the measurement of a transvalvular bioimpedance, and is also influenced by the self-impedance of the septum tissues.

The analysis of the cardiac contractility signal provided by sensor 56 can be done in the following way (the example of a PEA sensor will be taken, but this teaching is fully transposable to the signals provided by an intracardiac bioimpedance sensor).

The device daily reveals the remarkable points of the signal, for example, the delay between the PEA I peak and PEA II peak, and the amplitude maxima of PEA I and PEA II peaks. These data are recorded in the device memories and processed on a daily basis (filtering, etc.). It is advantageous to operate a long-term smoothing (typically, over one week) of the PEA amplitudes so as to prevent erratic variations; the criterion for triggering the alert can, for example, be of the type comparing the weekly average of the PEA I amplitude values to a given threshold such as:

$$(1/7) \sum_{i=j-7}^{i=j} (\text{Ampli\_PEAI}_{(i)}) < \text{Delay\_Limit}$$

The alert is then triggered when the threshold is crossed.

Another option compares the average of PEA I amplitudes over the last seven days, for example, with the corresponding average over the last 21 days. If the average over 7 days is lower than a given percentage of the average over the last 21 days:

$$(1/7) \sum_{i=j-7}^{i=j} (\text{Ampli\_PEAI}_{(i)}) < \text{Percent\_Ampli} * (1/21) \sum_{i=j-21}^{i=j} (\text{Ampli\_PEAI}_{(i)})$$

then an alert is triggered.

In the examples above, the parameters Delay_Limit or Percent_Ampli correspond to the "set of criteria of cardiac contractility", with (as in the case of the set of criteria of clinical status) the possibility to define at least two sets of criteria each providing a different sensitivity and specificity.

The implementation of the transfer functions 50 and 54 thus produce, through applying the sets of criteria {S1, S2} and {S'1, S'2}, four possibilities (binary signals alert/no alert), which are combined together in block 60 following the truth table illustrated on FIG. 8, so as to provide a composite output alert signal.

In a preferred embodiment, the composite alert that is produced (or not) by the cross-analysis stage 60 is an alert with several levels: "no action", "level 1 alert" or "level 2 alert". Also, when an alert is produced, this alert can be further differentiated in sub-levels so as to indicate in a finer manner, the cause of triggering the alert.

Hence:

the case "no action" corresponds to an absence of alert both at the output of transfer function 50 for analysis of the clinical status, and transfer function 54 for analysis of the cardiac contractility. In such case, the device of course produces no alert; it simply records the daily data. It will be the same when one of the transfer functions 50 or 54 does not produce any alert, and the other produces an alert, but only upon the basis of criteria S1 (or S'1 respectively), that is, the set of criteria with maximum sensitivity. In such case, one can reasonably suspect a false positive and then prevent from uselessly triggering an alert.

The case "level 1 alert" corresponds to a situation where transfer functions 50 and 54 both deliver an alert upon the basis of the sets of criteria S1 and S'1 (sensitive but a few specific criteria), or if one of the transfer functions 50 or 54 does not produce any alert but the other produces an alert upon the basis of the set of criteria S2 (or S'2 respectively), that is, the set of criteria with high specificity. In such cases, one can suspect a decompensation with a daily impact on the patient. The alert at this level will for instance lead to automatic sending of a message to the practitioner so as to ask him to get in contact with the patient following a serious degradation of the patient's daily status, for a reason other than cardiac decompensation (case of the "level 1a alert" in truth table of FIG. 8), or emission of an alert toward the patient so as to warn him that he shall urgently seek medical care due to advanced cardiac decompensation ("1b alert").

The case "level 2 alert", a more serious alert, corresponds to a situation where transfer functions 50 and 54 both produce alerts, on the basis of sets of criteria S2 and S'2. In such case, the patient shall be immediately alerted, for example, by activation of a buzzer or vibrator, to seek urgently medical care due to advanced cardiac decompensation. A level 2 alert is also produced when one of the transfer functions has produced an alert upon the basis of a criterion with high specificity S2 (or S'2 respectively), the other transfer function having produced an alert only upon the basis of a criterion with high sensitivity S'1 (or S1, respectively). The patient shall then be alerted to seek urgently medical care due to onset of cardiac decompensation, with daily impact on his activity ("level 2a alert") or with no daily impact on his activity ("2b alert").

FIG. 9 shows, in a bidimensional space, the position of the respective indices of clinical status, and cardiac contractility, calculated on a daily basis, as a function of the sets of criteria {S1, S2} and {S'1, S'2}. In this space, an increasing ordinate or abscissa indicate a higher specificity, with a correlative lower sensitivity.

If it only referred to an analysis of the clinical status (transfer function 50 based upon physiologic MV and physical G signals), only the situations corresponding to the points located within Zone A are likely to lead to an alert. In order to obtain an alert with a point located within Zone B, the specificity of the sensing threshold should have been lowered from S2 down to S1, with correlative triggering of alerts for the points located within zone C, these alerts presumably corresponding to false positives. Finally, a point located within Zone D would never be diagnosed as likely to lead to an alert, thus corresponding to a false negative.

The combined analysis of clinical status and cardiac contractility with, in each case, the application of at least two different criteria, allows to trigger alerts for points located within zones B and D, without triggering alerts for those within Zone C.

In the alternative or in addition, it is possible to use a "state machine" type process for processing the data of clinical status and/or cardiac contractility, in which the results of the comparisons with the various thresholds are applied to a state transition system with a memory, which takes the decision to trigger an alert as a function of a more complex evolution scheme. Some other types of analyses, more complex, can also be implemented so as to improve further the quality of the detection process, for example, correlation techniques, signal morphology analysis, frequential analysis, wavelet analysis, etc.

One skilled in the art will appreciate that the present invention can be practiced by embodiments other than those disclosed, which are presented for purposes of illustration and not of limitation.

I claim:

1. An active implantable medical device having a diagnostic function, comprising:

means for measuring a predominantly physiologic corporal parameter of a patient and providing a physiologic signal representative of said patient's metabolic need;

means for measuring a predominantly physical corporal parameter of said patient and providing a physical signal representative of said patient's activity level;

means for discriminating between phases of exercise and rest, operative in response to said physiologic and physical signals, and generating an activity index;

means for evaluating a clinical status of the patient and generating a clinical status index through applying a first set of criteria (S1, S2) to the physiologic and physical signals and the activity index;

means for measuring a hemodynamic parameter of said patient and providing a hemodynamic signal representative of the patient's cardiac contractility;

means for evaluating said patient's cardiac contractility, and generating a cardiac contractility index through applying a second set of criteria (S'1,S'2) to the hemodynamic signal; and means for cross analysis, receiving as an input said clinical status index, said cardiac contractility index, and generating as an output a preventive alert signal that is function of the respective values of the clinical status index and the cardiac contractility index.

2. The device of claim 1, wherein the means for measuring a predominantly physiological corporal parameter comprises a minute ventilation (MV) sensor.

3. The device of claim 1, wherein the means for measuring a hemodynamic parameter comprises means for measuring an endocardial acceleration (PEA).

4. The device of claim 3 wherein the means for measuring an endocardial acceleration comprises an accelerometer coupled to an endocardial lead.

5. The device of claim 1, wherein the means for measuring a hemodynamic parameter comprises means for measuring an intracardiac impedance.

6. The device of claim 1, wherein the means for cross analysis comprises boolean means implementing a table univalently providing, for each possible combination of said clinical status index and said cardiac contractility index, a corresponding value for the preventive alert signal.

7. The device of claim 1, wherein the means for evaluating the clinical status and the means for evaluating said patient's cardiac contractility comprise means for concurrently applying at least two sets of criteria including the first set of criteria and the second set of criteria, said at least two sets of criteria corresponding to at least one set of criteria with a high sensitivity (S1, S'1) and at least one set of criteria with a high specificity (S2, S'2).

8. The device of claim 7, wherein the clinical status index and the cardiac contractility index comprise boolean indices set to a "no alert" value when no set of criteria is fulfilled, a "first level alert" value when the set of criteria with the high sensitivity is fulfilled, and a "second level alert" value when the set of criteria with the high specificity is fulfilled.

9. The device of claim 8, wherein the preventive alert signal is a boolean signal set to said "no alert" value when:
the clinical status index and the cardiac contractility index are both set to the "no alert" value,
the clinical status index is set to the "first level alert" value and the cardiac contractility index is set to the "no alert" value, or
the clinical status index is set to the "no alert" value and the cardiac contractility index is set to the "first level alert" value.

10. The device of claim 8, wherein the preventive alert signal is a boolean signal set to said "first level alert" value when:
the clinical status index and the cardiac contractility index are both set to the "first level alert" value,
the clinical status index is set to the "second level value" and the cardiac contractility index is set to the "no alert" value, or
the clinical status index is set to the "no alert" value and the cardiac contractility index is set to the "second level alert" value.

11. The device of claim 8, wherein the preventive alert signal is a boolean signal set to said "second level alert" when:
the clinical status index and the cardiac contractility index are both set to the "second level alert" value,
the clinical status index is set to the "second level alert" value and the cardiac contractility index is set to the "first level alert" value, or
the clinical status index is set to the "first level alert" value and the cardiac contractility index is set to the "second level alert" value.

12. The device of claim 1, wherein the means for evaluating the clinical status comprises means for evaluating a meta-index, based upon the successive values taken by the clinical status index, and for applying the first set of criteria to said meta-index.

13. The device of claim 1, further comprising means for evaluating with a daily periodicity, said clinical status index and said cardiac contractility index.

14. The device of claim 1, wherein said device further comprises means for selecting a cardiac therapy selected from among the group consisting of pacing, resynchronization, defibrillation and/or cardioversion.

* * * * *